US008293710B2

(12) United States Patent
Wu et al.

(10) Patent No.: US 8,293,710 B2
(45) Date of Patent: Oct. 23, 2012

(54) METHOD FOR TREATING WOUNDS USING AN EGF-LIKE DOMAIN OF THROMBOMODULIN

(75) Inventors: Hua-Lin Wu, Tainan (TW); Guey-Yueh Shi, Tainan (TW)

(73) Assignee: Blue Blood Biotech Corp., Taipei (TW)

(*) Notice: Subject to any disclaimer, the term of this patent is extended or adjusted under 35 U.S.C. 154(b) by 341 days.

(21) Appl. No.: 11/361,560

(22) Filed: Feb. 24, 2006

(65) Prior Publication Data

US 2006/0148706 A1 Jul. 6, 2006

Related U.S. Application Data

(63) Continuation-in-part of application No. 11/149,378, filed on Jun. 9, 2005, now abandoned.

(60) Provisional application No. 60/641,213, filed on Jan. 3, 2005.

(51) Int. Cl.
*A61K 38/18* (2006.01)

(52) U.S. Cl. ......... 514/12; 514/2; 435/252.33; 424/94.3

(58) Field of Classification Search ........................ None
See application file for complete search history.

(56) References Cited

U.S. PATENT DOCUMENTS

| 5,583,102 | A  | * | 12/1996 | Lentz et al. .................. 514/13.7 |
| 6,635,249 | B1 | * | 10/2003 | Marchionni et al. ........ 424/145.1 |
| 7,087,721 | B2 | * | 8/2006  | Wu et al. ......................... 530/381 |
| 2002/0111296 | A1 | * | 8/2002 | Festoff et al. ..................... 514/8 |

FOREIGN PATENT DOCUMENTS

JP          9020677        1/1997

OTHER PUBLICATIONS

Wells, Biochemistry, vol. 29, pp. 8509-8517, 1990.*
Carson et al. (Cancer Research vol. 61, pp. 6649-6655, Sep. 2001.*
Peterson et al. (Am. J. Pathol., 1999, vol. 155, pp. 1569-1575).*
Tohda, Gen et al., Expression of Thrombomodulin in Atherosclerotic Lesions and Mitogenic Activity of Recombinant Thrombomodulin in Vascular Smooth Muscle Cells, *Arteriosclerosis, Thrombosis, and Vascular Biology* (1998) vol. 18 p. 1861-1869.
Kumar R. et al., Regulation of distinct steps of angiogenesis by different angiogenic molecules, Int J. Oncol., Apr. 1998; 12(4):749-57.
Suzuki K. et al., Isolation and characterization of thrombomodulin from bovine lung, Biochim Biophys Acta. Jul. 16, 1986; 882(3):343-52.
Wilhelm S et al., Thrombomodulin, a receptor for the serine protease thrombin, is decreased in primary tumors and metastases but increased in ascitic fluids of patients with advanced ovarian cancer FIGO IIIc., Int J Oncol. Oct. 1998; 13(4):645-51.
Shi et al., Evidence of Human Thrombomodulin Domain as a Novel Angiogenic Factor, Circulation (2005) 111:1627-1636.
Suzuki et al., Structure and expression of human thrombomodulin, a thrombin receptor on endothelium acting as a cofactor for protein C activation, EMBO Journal vol. 6, No. 7 pp. 1891-1897 (1987).
Boffa et al., Preservation of Thrombomodulin Antigen on Vascular and Extravascular Surfaces, The Journal of Histochemistry and Cytochemistry vol. 35, No. 11, pp. 1267-1276 (1987).
Yamamoto et al., Urinary Thrombomodulin, Its Isolation and Characterization, J. Biochem. 113, 483-440 (1993).
U.K. Laemmli, Cleavage of Structural Proteins during the Assembly of the Head of Bacteriophage T4, Nature vol. 227, Aug. 15, 1970.
Oh et al., Identification of angiogenic properties of insulin-like growth factor II in in vitro angiogenesis models, Pub Med., Br J Cancer, Jan. 2000; 82(2):385-91.
Kenyon et al., A Model of Angiogenesis in the Mouse Cornea, Investigative Ophthalmology & Visual Science, Jul. 1996, vol. 37, No. 8.
Passaniti, et al., A Simple, Quantitative Method for Assessing Angiogenesis and Antiangiogenic Agents Using Reconstituted Basement Membrane, Heparin, and Fibroblast Growth Factor, Laboratory Investigation, Vo. 67, No. 4, p. 519, (1992).
Shirai et al., Gene Structure of Human Thrombomodulin, a Cofactor for Thrombin-Catalyzed Activation of Protein C, J. Biochem. 103, 281-285 (1988).
Kurosawa et al., Preparation of Thrombomodulin From Human Placenta, Human Thrombomodulin, vol. 37, No. 3, pp. 353-364 (1985).
Tezuka et al., Expression of Thrombomodulin in Esophageal Squamous Cell Carcinoma and Its Relationship to Lymph Node Metastasis, Cancer Research 55, pp. 4196-4200 Sep. 15, 1995.
Seffernick et al. (J. Bacteriology, vol. 183, pp. 2405-2410, 2001).
Hunter et al. (Protein Science, vol. 4 issue 10, 1995).
Australian Examiner's first report on patent application No. 2006258230 by Chuan-Chi dated Apr. 30, 2009.
Australian Patent Office Written Opinion dated Jun. 19, 2009.
Chen, Y.H. et al. "The role of thrombomodulin in wound healing process" Master Thesis, Cheng-Kung University, Tainan, Taiwan. Jul. 2004 (Abstract, Fig. 5, 6, 7, 8, 9, sequence; English translations attached).
Benedetta A. Sampoli Benitez, et al., Structure of the Fifth EGF-like Domain of Thrombomodulin: An EGF-like Domain with a Novel Disulfide-Bonding Pattern, *J. Mol. Biol.* (1997) 273, 913-926.
Written Opinion, Singapore Application No. 0719056-4, in the name of Blue Blood Biotech Corp. Application filed on Apr. 26, 2006.

* cited by examiner

*Primary Examiner* — Hope Robinson
(74) *Attorney, Agent, or Firm* — Hsiu-Ming Saunders; Intellectual Property Connections, Inc.

(57) ABSTRACT

The invention relates to a method for treatment of wound healing, comprising administering to a patient in need of such treatment with an effective amount of a polypeptide comprising amino acid sequence or a conservative variant thereof having EGF-like domain of thrombomodulin. The invention also relates to a composition for the use of accelerating wound healing, comprising a polypeptide comprising amino acid sequence or a conservative variant thereof having EGF-like domain of thrombomodulin.

17 Claims, 4 Drawing Sheets

FIG.1

(n=3, *p < 0.05 vs control; #p < 0.05 vs TMD23)

SEQUENCE LISTING

```
<160> NUMBER OF SEQ ID NOS: 2

<210> SEQ ID NO 1
<211> LENGTH: 4593
<212> TYPE: DNA
<213> ORGANISM: Homo sapiens
<220> FEATURE:
<221> NAME/KEY: CDS
<222> LOCATION: (719)..(2443)

<400> SEQUENCE: 1
```

```
                                                     -continued ggatccagct gtctctcctt gcgatcctgt cttcggggaa gtccacgtcc taggcaggtc    60
ctcccaaagt gcccttggtg ccgatcaccc ctcccagcgt cttgcaggtc ctgtgcacca   120
cctcccccac tccccattca aagccctctt ctctgaagtc tccggttccc agagctcttg   180
caatccaggc tttccttgga agtggctgta acatgtatga aaagaaagaa aggaggacca   240
agagatgaaa gagggctgca cgcgtggggg cccgagtggt gggcggggac agtcgtcttg   300
ttacaggggt gctggccttc cctggcgcct gccctgtcg gccccgcccg agaacctccc   360
tgcgccaggg cagggtttac tcatcccggc gaggtgatcc catgcgcgag ggcgggcgca   420
agggcggcca gagaacccag caatccgagt atgcggcatc agcccttccc accaggcact   480
tccttccttt tcccgaacgt ccagggaggg agggccgggc acttataaac tcgagccctg   540
gccgatccgc atgtcagagg ctgcctcgca ggggctgcgc gcagcggcaa gaagtgtctg   600
ggctgggacg gacaggagag gctgtcgcca tcggcgtcct gtgccctct gctccggcac   660 ggccctgtcg cagtgcccgc gctttccccg gcgcctgcac gcggcgcgcc tgggtaac    718 atg ctt ggg gtc ctg gtc ctt ggc gcg ctg gcc ctg gcc ggc ctg ggg    766
Met Leu Gly Val Leu Val Leu Gly Ala Leu Ala Leu Ala Gly Leu Gly
  1               5                  10                  15 ttc ccc gca ccc gca gag ccg cag ccg ggt ggc agc cag tgc gtc gag    814
Phe Pro Ala Pro Ala Glu Pro Gln Pro Gly Gly Ser Gln Cys Val Glu
                 20                  25                  30 cac gac tgc ttc gcg ctc tac ccg ggc ccc gcg acc ttc ctc aat gcc    862
His Asp Cys Phe Ala Leu Tyr Pro Gly Pro Ala Thr Phe Leu Asn Ala
             35                  40                  45 agt cag atc tgc gac gga ctg cgg ggc cac cta atg aca gtg cgc tcc    910
Ser Gln Ile Cys Asp Gly Leu Arg Gly His Leu Met Thr Val Arg Ser
         50                  55                  60 tcg gtg gct gcc gat gtc att tcc ttg cta ctg aac ggc gac ggc ggc    958
Ser Val Ala Ala Asp Val Ile Ser Leu Leu Leu Asn Gly Asp Gly Gly
 65                  70                  75                  80 gtt ggc cgc cgg cgc ctc tgg atc ggc ctg cag ctg cca ccc ggc tgc   1006
Val Gly Arg Arg Arg Leu Trp Ile Gly Leu Gln Leu Pro Pro Gly Cys
                 85                  90                  95 ggc gac ccc aag cgc ctc ggg ccc ctg cgc ggc ttc cag tgg gtt acg   1054
Gly Asp Pro Lys Arg Leu Gly Pro Leu Arg Gly Phe Gln Trp Val Thr
            100                 105                 110 gga gac aac aac acc agc tat agc agg tgg gca cgg ctc gac ctc aat   1102
Gly Asp Asn Asn Thr Ser Tyr Ser Arg Trp Ala Arg Leu Asp Leu Asn
        115                 120                 125 ggg gct ccc ctc tgc ggc ccg ttg tgc gtc gct gtc tcc gct gct gag   1150
Gly Ala Pro Leu Cys Gly Pro Leu Cys Val Ala Val Ser Ala Ala Glu
    130                 135                 140 gcc act gtg ccc agc gag ccg atc tgg gag gag cag cag tgc gaa gtg   1198
Ala Thr Val Pro Ser Glu Pro Ile Trp Glu Glu Gln Gln Cys Glu Val
145                 150                 155                 160 aag gcc gat ggc ttc ctc tgc gag ttc cac ttc cca gcc acc tgc agg   1246
Lys Ala Asp Gly Phe Leu Cys Glu Phe His Phe Pro Ala Thr Cys Arg
                165                 170                 175 cca ctg gct gtg gag ccc ggc gcc gcg gct gcc gtc tcg atc acc   1294
Pro Leu Ala Val Glu Pro Gly Ala Ala Ala Ala Val Ser Ile Thr
            180                 185                 190 tac ggc acc ccg ttc gcg gcc cgc gga gcg gac ttc cag gcg ctg ccg   1342
Tyr Gly Thr Pro Phe Ala Ala Arg Gly Ala Asp Phe Gln Ala Leu Pro
            195                 200                 205 gtg ggc agc tcc gcc gcg gtg gct ccc ctc ggc tta cag cta atg tgc   1390
Val Gly Ser Ser Ala Ala Val Ala Pro Leu Gly Leu Gln Leu Met Cys
            210                 215                 220
```

```
acc gcg ccg ccc gga gcg gtc cag ggg cac tgg gcc agg gag gcg ccg    1438
Thr Ala Pro Pro Gly Ala Val Gln Gly His Trp Ala Arg Glu Ala Pro
225                 230                 235                 240 ggc gct tgg gac tgc agc gtg gag aac ggc ggc tgc gag cac gcg tgc    1486
Gly Ala Trp Asp Cys Ser Val Glu Asn Gly Gly Cys Glu His Ala Cys
                245                 250                 255 aat gcg atc cct ggg gct ccc cgc tgc cag tgc cca gcc ggc gcc gcc    1534
Asn Ala Ile Pro Gly Ala Pro Arg Cys Gln Cys Pro Ala Gly Ala Ala
            260                 265                 270 ctg cag gca gac ggg cgc tcc tgc acc gca tcc gcg acg cag tcc tgc    1582
Leu Gln Ala Asp Gly Arg Ser Cys Thr Ala Ser Ala Thr Gln Ser Cys
        275                 280                 285 aac gac ctc tgc gag cac ttc tgc gtt ccc aac ccc gac cag ccg ggc    1630
Asn Asp Leu Cys Glu His Phe Cys Val Pro Asn Pro Asp Gln Pro Gly
    290                 295                 300 tcc tac tcg tgc atg tgc gag acc ggc tac cgg ctg gcc gcc gac caa    1678
Ser Tyr Ser Cys Met Cys Glu Thr Gly Tyr Arg Leu Ala Ala Asp Gln
305                 310                 315                 320 cac cgg tgc gag gac gtg gat gac tgc ata ctg gag ccc agt ccg tgt    1726
His Arg Cys Glu Asp Val Asp Asp Cys Ile Leu Glu Pro Ser Pro Cys
                325                 330                 335 ccg cag cgc tgt gtc aac aca cag ggt ggc ttc gag tgc cac tgc tac    1774
Pro Gln Arg Cys Val Asn Thr Gln Gly Gly Phe Glu Cys His Cys Tyr
            340                 345                 350 cct aac tac gac ctg gtg gac ggc gag tgt gtg gag ccc gtg gac ccg    1822
Pro Asn Tyr Asp Leu Val Asp Gly Glu Cys Val Glu Pro Val Asp Pro
        355                 360                 365 tgc ttc aga gcc aac tgc gag tac cag tgc cag ccc ctg aac caa act    1870
Cys Phe Arg Ala Asn Cys Glu Tyr Gln Cys Gln Pro Leu Asn Gln Thr
    370                 375                 380 agc tac ctc tgc gtc tgc gcc gag ggc ttc gcg ccc att ccc cac gag    1918
Ser Tyr Leu Cys Val Cys Ala Glu Gly Phe Ala Pro Ile Pro His Glu
385                 390                 395                 400 ccg cac agg tgc cag atg ttt tgc aac cag act gcc tgt cca gcc gac    1966
Pro His Arg Cys Gln Met Phe Cys Asn Gln Thr Ala Cys Pro Ala Asp
                405                 410                 415 tgc gac ccc aac acc cag gct agc tgt gag tgc cct gaa ggc tac atc    2014
Cys Asp Pro Asn Thr Gln Ala Ser Cys Glu Cys Pro Glu Gly Tyr Ile
            420                 425                 430 ctg gac gac ggt ttc atc tgc acg gac atc gac gag tgc gaa aac ggc    2062
Leu Asp Asp Gly Phe Ile Cys Thr Asp Ile Asp Glu Cys Glu Asn Gly
        435                 440                 445 ggc ttc tgc tcc ggg gtg tgc cac aac ctc ccc ggt acc ttc gag tgc    2110
Gly Phe Cys Ser Gly Val Cys His Asn Leu Pro Gly Thr Phe Glu Cys
    450                 455                 460 atc tgc ggg ccc gac tcg gcc ctt gtc cgc cac att ggc acc gac tgt    2158
Ile Cys Gly Pro Asp Ser Ala Leu Val Arg His Ile Gly Thr Asp Cys
465                 470                 475                 480 gac tcc ggc aag gtg gac ggt ggc gac agc ggc tct ggc gag ccc ccg    2206
Asp Ser Gly Lys Val Asp Gly Gly Asp Ser Gly Ser Gly Glu Pro Pro
                485                 490                 495 ccc agc ccg acg ccc ggc tcc acc ttg act cct ccg gcc gtg ggg ctc    2254
Pro Ser Pro Thr Pro Gly Ser Thr Leu Thr Pro Pro Ala Val Gly Leu
            500                 505                 510 gtg cat tcg ggc ttg ctc ata ggc atc tcc atc gcg agc ctg tgc ctg    2302
Val His Ser Gly Leu Leu Ile Gly Ile Ser Ile Ala Ser Leu Cys Leu
        515                 520                 525 gtg gtg gcg ctt ttg gcg ctc ctc tgc cac ctg cgc aag aag cag ggc    2350
Val Val Ala Leu Leu Ala Leu Leu Cys His Leu Arg Lys Lys Gln Gly
    530                 535                 540
```

| | | |
|---|---|---|
| gcc gcc agg gcc aag atg gag tac aag tgc gcg gcc cct tcc aag gag<br>Ala Ala Arg Ala Lys Met Glu Tyr Lys Cys Ala Ala Pro Ser Lys Glu<br>545                          550                    555                    560 | | 2398 |
| gta gtg ctg cag cac gtg cgg acc gag cgg acg ccg cag aga ctc<br>Val Val Leu Gln His Val Arg Thr Glu Arg Thr Pro Gln Arg Leu<br>                  565                    570                    575 | | 2443 |
| tgagcggcct ccgtccagga gcctggctcc gtccaggagc ctgtgcctcc tcaccccag | | 2503 |
| ctttgctacc aaagcacctt agctggcatt acagctggag aagaccctcc ccgcaccccc | | 2563 |
| caagctgttt tcttctattc catggctaac tggcgagggg gtgattagag ggaggagaat | | 2623 |
| gagcctcggc ctcttccgtg acgtcactgg accactgggc aatgatggca attttgtaac | | 2683 |
| gaagacacag actgcgattt gtcccaggtc ctcactaccg ggcgcaggag ggtgagcgtt | | 2743 |
| attggtcggc agccttctgg gcagaccttg acctcgtggg ctagggatga ctaaaatatt | | 2803 |
| tatttttttt aagtatttag gttttgttt gttcctttg tcttacctg tatgtctcca | | 2863 |
| gtatccactt gcacagctc tccggtctct ctctctctac aaactcccac ttgtcatgtg | | 2923 |
| acaggtaaac tatcttggtg aatttttttt tcctagccct ctcacattta tgaagcaagc | | 2983 |
| cccacttatt cccattctt cctagttttc tcctcccagg aactgggcca actcacctga | | 3043 |
| gtcaccctac ctgtgcctga ccctacttct tttgctctta gctgtctgct cagacagaac | | 3103 |
| ccctacatga acagaaaca aaacactaa aataaaaat ggccatttgc ttttcacca | | 3163 |
| gatttgctaa tttatcctga aatttcagat tcccagagca aaataatttt aaacaaggt | | 3223 |
| tgagatgtaa aaggtattaa attgatgttg ctggactgtc atagaaatta cacccaaaga | | 3283 |
| ggtatttatc tttactttta aacagtgagc ctgaattttg ttgctgtttt gatttgtact | | 3343 |
| gaaaaatggt aattgttgct aatcttctta tgcaatttcc ttttttgtta ttattactta | | 3403 |
| tttttgacag tgttgaaaat gttcagaagg ttgctctaga ttgcgagaag agacaaacac | | 3463 |
| ctcccaggag acagttcaag aaagcttcaa actgcatgat tcatgccaat tagcaattga | | 3523 |
| ctgtcactgt tccttgtcac tggtagacca aaataaaacc agctctactg gtcttgtgga | | 3583 |
| attgggagct tgggaatgga tcctggagga tgcccaatta gggcctagcc ttaatcaggt | | 3643 |
| cctcagagaa tttctaccat ttcagagagg cctttggaa tgtggcccct gaacaagaat | | 3703 |
| tggaagctgc cctgcccatg ggagctggtt agaaatgcag aatcctaggc tccaccccat | | 3763 |
| ccagttcatg agaatctata tttaacaaga tctgcagggg gtgtgtctgc tcagtaattt | | 3823 |
| gaggacaacc attccagact gcttccaatt ttctggaata catgaaatat agatcagtta | | 3883 |
| taagtagcag gccaagtcag gcccttattt tcaagaaact gaggaattt ctttgtgtag | | 3943 |
| ctttgctctt tggtagaaaa ggctaggtac acagctctag acactgccac acagggtctg | | 4003 |
| caaggtcttt ggttcagcta agctaggaat gaaatcctgc ttcagtgtat ggaaataaat | | 4063 |
| gtatcataga aatgtaactt ttgtaagaca aaggttttcc tcttctattt tgtaaactca | | 4123 |
| aaatatttgt acatagttat ttatttattg gagataatct agaacacagg caaatcctt | | 4183 |
| gcttatgaca tcacttgtac aaaataaaca aataacaatg tgctctcggg ttgtgtgtct | | 4243 |
| gttcattttc ctcccctcagt gccctcattt tatgtcatta aatggggctc acaaaccatg | | 4303 |
| caaatgctat gagatgcatg gagggctgcc ctgtacccca gcacttgtgt tgtctggtga | | 4363 |
| tggcaccatc tctgattttc aaagcttttt ccagaggcta ttattttcac tgtagaatga | | 4423 |
| tttcatgcta tctctgtgtg cacaaatatt tattttcttt ctgtaaccat aacaacttca | | 4483 |
| tatatgagga cttgtgtctc tgtgctttta aatgcataaa tgcattatag gatcatttgt | | 4543 |
| tggaatgaat taaataaacc cttcctgggg catctggcga atcccagctg | | 4593 |

<210> SEQ ID NO 2
<211> LENGTH: 575
<212> TYPE: PRT
<213> ORGANISM: Homo sapiens

<400> SEQUENCE: 2

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

-continued

```
Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
    450                 455                 460

Ile Cys Gly Pro Asp Ser Ala Leu Val Arg His Ile Gly Thr Asp Cys
465                 470                 475                 480

Asp Ser Gly Lys Val Asp Gly Gly Asp Ser Gly Ser Gly Glu Pro Pro
            485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575
```

METHOD FOR TREATING WOUNDS USING AN EGF-LIKE DOMAIN OF THROMBOMODULIN

CROSS REFERENCE TO RELATED APPLICATIONS

This application is a continuation-in-part of and claims priority to U.S. patent application Ser. No. 11/149,378 filed on Jun. 9, 2005, which status is abandoned and claims priority to U.S. No. 60/641,213 filed on Jan. 3, 2005.

BACKGROUND OF THE INVENTION

Field of the Invention

The invention relates to a method and a composition for the use of accelerating wound healing.

Angiogenesis and Thrombomodulin

Although several molecules are known in the art as useful therapeutic agents for the treatment of diseases and disorders having as a symptom thereof abnormal clotting in critical blood vessels, there remains a need in the art for compositions and methods which are useful for the treatment of such diseases as well as for the treatment of diseases and disorders having as symptoms abnormally high or abnormally low angiogenic activity. Such diseases and conditions include the following: cardiovascular diseases and conditions such as hypotension, hypertension and atherosclerosis; thrombotic conditions such as stroke, heart attack and post angioplasty stenting; angiogenic disorders; respiratory diseases and conditions such as pulmonary fibrosis and asthma; diseases and disorders related to tumor cell invasion, angiogenesis and metastasis; wound healing and clotting disorders and reproductive disorders such as premature uterine contraction and impotence.

In present day, a number of biomolecules, which induce or promote angiogenesis in tissues, have been identified. The most prominent of these are: growth factors such as vascular endothelial growth factor (VEGF), fibroblast growth factor (FGF), epidermal growth factor (EGF), platelet-derived growth factors (PDGFs) and transforming growth factors (TGFs). Absence of the blood-clotting regulator thrombomodulin causes embryonic lethality in mice before development of a functional cardiovascular system. (Proc. Natl. Acad. Sci. USA. 1995; 92:850-854; and J P Cooke et al, Circulation 105 (2002) 2133). The current approaches aimed at promoting angiogenesis in the related field can be summarized into three main categories: (i) delivery of angiogenic growth factors using synthetic and natural polymeric scaffolds; (ii) delivery of plasmids containing DNA that encodes for angiogenic proteins; and (iii) combined delivery of angiogenic molecules and endothelial cell transplantation.

In accordance to the related arts, another report (Shi C S et al., Evidence of Human Thrombomodulin Domain as a Novel Angiogenic Factor. Circulation. Apr. 5, 2005; 111(13):1627-36) proposed loading the delivery systems with human recombinant thrombomodulin molecules instead of growth factors. It is proposed that the loaded human recombinant thrombomodulin can be released under physiological conditions, thus promoting localized, rapid angiogenesis.

Thrombomodulin is an anticoagulant, endothelial-cell-membrane glycoprotein. Recombinant thrombomodulin proteins, TMD2 (containing six EGF-like structures) and TMD23 (containing TMD2 and a serine-threonine rich domain), exhibit mitogenic activity.

The previous study (Shi C S et al., Evidence of Human Thrombomodulin Domain as a Novel Angiogenic Factor. Circulation. Apr. 5, 2005; 111(13):1627-36) have revealed the recombinant domain's novel angiogenic effects using in vitro and in vivo models. It was shown that TMD23 had higher activity than TMD2 in stimulating DNA synthesis in cultured human umbilical vein endothelial cells (HUVECs). Additionally, TMD23 stimulated chemotactic motility and capillary-like tube formation in HUVECs, an effect mediated through phosphorylation of extracellular signal-regulated kinase 1/2 and p38 mitogen-activated protein kinase and the phosphatidylinositol-3 kinase/Akt/endothelial nitric oxide synthase pathway. TMD23 also stimulated endothelial-cell expression of matrix metalloproteinases and plasminogen activators, which mediated extracellular proteolysis leading to endothelial-cell invasion and migration during angiogenesis. Moreover, TMD23-containing implants in rat cornea induced ingrowth of new blood vessels from the limbus. Using the murine angiogenesis assay, TMD23 not only induced neovascularization coinjected with Matrigel and heparin but also enhanced angiogenesis in Matrigel containing melanoma A2058 cells in nude mice. In conclusion, the recombinant thrombomodulin domain TMD23 enhanced the angiogenic response in vitro and in vivo.

Wound Healing

The wound healing process has 3 phases. They are the inflammatory phase, the proliferative phase, and the maturational phase.

The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, potent vasoconstrictors. This initial response helps to limit hemorrhage. After a short period, capillary vasodilatation occurs secondary to local histamine release, and the cells of inflammation are able to migrate to the wound bed.

Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

The inflammatory phase continues, and more immune response cells migrate to the wound. The second response cell to migrate to the wound, the neutrophil, is responsible for debris scavenging, complement-mediated opsonization of bacteria, and bacteria destruction via oxidative burst mechanisms (ie, superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, ie, the proliferative phase.

The second stage of wound healing is the proliferative phase. Epithelialization, angiogenesis, granulation tissue formation, and collagen deposition are the principal steps in this anabolic portion of wound healing. Epithelialization occurs early in wound repair. If the basement membrane remains intact, the epithelial cells migrate upwards in the normal pattern. This is equivalent to a first-degree skin burn. The epithelial progenitor cells remain intact below the wound, and the normal layers of epidermis are restored in 2-3 days. If the basement membrane has been destroyed, similar to a second- or third-degree burn, then the wound is reepithelialized from the normal cells in the periphery and from the skin appendages, if intact (eg, hair follicles, sweat glands).

Angiogenesis, stimulated by TNF-alpha, is marked by endothelial cell migration and capillary formation. The new capillaries deliver nutrients to the wound and help maintain the granulation tissue bed. The migration of capillaries into the wound bed is critical for proper wound healing. The granulation phase and tissue deposition require nutrients supplied by the capillaries, and failure for this to occur results in a chronically unhealed wound. Mechanisms for modifying angiogenesis are under study and have significant potential to improve the healing process.

The final part of the proliferative phase is granulation tissue formation. Fibroblasts differentiate and produce ground substance and then collagen. The ground substance is deposited into the wound bed; collagen is then deposited as the wound undergoes the final phase of repair. Many different cytokines are involved in the proliferative phase of wound repair. The steps and the exact mechanism of control have not been elucidated. Some of the cytokines include PDGF, insulinlike growth factor (IGF), and EGF. All are necessary for collagen formation.

The final phase of wound healing is the maturational phase. The wound undergoes contraction, ultimately resulting in a smaller amount of apparent scar tissue. The entire process is a dynamic continuum with an overlap of each phase and continued remodeling. The wound reaches maximal strength at one year, with a tensile strength that is 30% of normal skin. Collagen deposition continues for a prolonged period, but the net increase in collagen deposition plateaus after 21 days.

Currently, cytokines have a limited role in clinical practice. The only currently available commercial product proven to be efficacious in randomized, double blind-studies is PDGF, available as recombinant human PDGF-BB. In multiple studies, recombinant human PDGF-BB has been demonstrated to reduce healing time and improve the incidence of complete wound healing in stage III and IV ulcers. Many other cytokines currently under study in vitro include TGF-beta, EGF, and IGF-1.

Proper wound healing involves a complex interaction of cells and cytokines working in concert. In recent years, more chemical mediators integral to this process have been identified. The sequential steps and specific processes have not been fully differentiated. When examining the process of wound healing, one should identify the major steps and know the important mediators.

Burn and Wound Healing

Burn is the injury resulting from exposure to heat, electricity, radiation (for example, sunburn and laser surgery), or caustic chemicals.

Three degrees of burn are commonly recognized. In first-degree burns the outer layer of skin, called epidermis, becomes red, sensitive to the touch, and often swollen. Medical attention is not required but application of an ointment may relieve the pain. Second-degree burns are characterized by the variable destruction of epidermis and the formation of blisters; nerve endings may be exposed. The more serious cases should be seen by a physician and care should be taken to avoid infection. Local therapy includes application of a chemical such as silver nitrate to produce a soft crust, reduce the threat of infection, and relieve the pain. Third-degree burns involve destruction of the entire thickness of skin and the underlying connective tissue. In the more severe cases underlying bones are also charred. The surface area involved is more significant than the depth of the burn. Shock must be prevented or counteracted; blood transfusion may be required to replace lost body fluids. Invasion of various bacteria must be prevented or cured by administering antibiotics and other drugs. Morphine may be employed to ease pain. Long-term treatment may include transplantation of natural or artificial skin grafts.

Diabetes Mellitus and Wound Healing

Diabetes mellitus is a group of metabolic diseases characterized by high blood sugar (glucose) levels, which result from defects in insulin secretion, or action, or both. Diabetes mellitus, commonly referred to as diabetes, means "sweet urine." Elevated levels of blood glucose (hyperglycemia) lead to spillage of glucose into the urine, hence the term sweet urine. Normally, blood glucose levels are tightly controlled by insulin, a hormone produced by the pancreas. Insulin lowers the blood glucose level. When the blood glucose elevates (for example, after eating food), insulin is released from the pancreas to normalize the glucose level. In patients with diabetes mellitus, the absence or insufficient production of insulin causes hyperglycemia. Diabetes mellitus is a chronic medical condition, meaning it can last a lifetime.

Diabetes may lead to several complications, including heart and blood vessel diseases, blindness, kidney failure and foot ulcers.

People with diabetes are at risk for foot injuries due to numbness caused by nerve damage (diabetic neuropathy) and low blood flow to the legs and feet. The most serious injury is a foot ulcer. Diabetic foot ulcers are at very high risk of becoming infected, and sometimes they cannot be healed. Non-healing foot ulcers are a frequent cause of amputation in people with diabetes.

FDA has cleared one gel product (becaplermin, or Regranex Gel) that is used as a treatment for diabetic foot ulcers. This product contains genetically engineered platelet-derived growth factor, one of the proteins the body produces to encourage new tissue growth. Clinical studies of the product indicated that the likelihood of complete ulcer closure, after up to 20 weeks of treatment, was greater when becaplermin is used.

Another product that helps in closing the wounds of slow healing ulcers in patients with diabetes is a skin substitute named DERMAGRAFT®. It is made from human cells known as fibroblasts that are placed on a dissolvable mesh material. When the mesh material is placed on the ulcer, it is gradually absorbed and the human cells grow and replace the damaged tissue in the ulcer.

SUMMARY OF THE INVENTION

The invention relates to a method for treatment of wound healing, comprising administering to a patient in need of such treatment with an effective amount of a polypeptide comprising amino acid sequence or a conservative variant thereof having EGF-like domain of thrombomodulin. The invention also relates to a composition for the use of accelerating wound healing, comprising a polypeptide comprising amino acid sequence or a conservative variant thereof having EGF-like domain of thrombomodulin.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE INVENTION

Thrombomodulin is an anticoagulant, endothelial-cell-membrane glycoprotein. A recombinant thrombomodulin domain containing six epidermal growth factor-like structures and serine-threonine rich domain exhibits mitogenic activity.

In the previous report (application Ser. No. 11/149,378) it was demonstrated that TMD23 could induce endothelial cell (HUVEC) migration and proliferation.

In the present invention, it was revealed that TMD23 could effectively enhance the migration of keratinocytes (HaCaT), the major cell type in the epidermis and the antibody against TMD23 could specifically inhibit keratinocyte migration.

Therefore, it was demonstrated the first time that TMD23 could enhance wound-healing process by stimulating keratinocyte migration.

Moreover, the animal experiments showed that TMD23 could enhance epidermis migration and extension into the wound area, therefore accelerating the wound closure. On the other hand, water evaporation rate from the wound opening was effectively reduced as well.

In conclusion, TM can effectively enhance the rate of wound healing.

The present invention relates to a method for treatment of wound healing, comprising administering to a patient in need of such treatment with an effective amount of a polypeptide comprising amino acid sequence or a conservative variant thereof having EGF-like domain of thrombomodulin. In the preferred embodiment, the polypeptide further comprises an operably linked polypeptide comprising amino acid sequence or a conservative variant of serine-threonine rich domain of thrombomodulin.

The method of the invention can be applied to the use of accelerating wound healing, wherein the wound is selected from the group consisting of incisions, lacerations, abrasions, puncture wounds, blisters, skin tears, donor or graft sites, acnes, contusions, hematoma, crushing injuries and injuries caused by dermabrasion or laser resurfacing.

The method of the invention can be used in patients with diabetes mellitus. In a preferred embodiment, the patient suffers from diabetes ulcers.

The method of the invention can also be applied when the wound is a burn resulted from fire, heat, radiation, electricity or dermatological surgery.

The method can be applied to reconstructive surgery.

In a preferred embodiment, the method is applied to a skin-carrying product selected from the group consisting of gel, cream, paste, lotion, spray, suspension, solution, dispersion salve, hydrogel and ointment formulation. In a more preferred embodiment, the skin-carrying product is administered to the patient in need of such treatment by applying onto skin, injection or electroporation.

The present invention also relates to a method for treatment of wound healing, comprising administering to a patient in need of such treatment with an effective amount of plasmid consisting of DNA encoding a polypeptide comprising amino acid sequence or a conservative variant thereof having EGF-like domain of thrombomodulin. In a preferred embodiment, the administration is by means of plasmid vaccine. In a more preferred embodiment, the administration is by route of intravenous (iv), subcutaneous (sc), intraperitoneal (ip), or intramuscular (im).

The present invention further relates to a composition for the use of accelerating wound healing, comprising a polypeptide comprising amino acid sequence or a conservative variant thereof having EGF-like domain of thrombomodulin. In the preferred embodiment, the polypeptide further comprises an operably linked polypeptide comprising amino acid sequence or a conservative variant of serine-threonine rich domain of thrombomodulin.

The composition of the invention can be applied to the use of accelerating wound healing, wherein the wound is selected from the group consisting of incisions, lacerations, abrasions, puncture wounds, blisters, skin tears, donor or graft sites, acnes, contusions, hematoma, crushing injuries and injuries caused by dermabrasion or laser resurfacing.

The composition of the invention can be used in patients with diabetes mellitus. In a preferred embodiment, the patient suffers from diabetes ulcers.

The composition of the invention can also be applied when the wound is a burn resulted from fire, heat, radiation, electricity or dermatological surgery.

In a preferred embodiment, the composition can be applied to reconstructive surgery.

In a preferred embodiment, the method is applied to a skin-carrying product selected from the group consisting of gel, cream, paste, lotion, spray, suspension, solution, dispersion salve, hydrogel and ointment formulation. In a more preferred embodiment, the skin-carrying product is administered to the patient in need of such treatment by applying onto skin, injection or electroporation.

Term Definition

The following definitions are offered for purposes of illustration, not limitation, in order to assist with understanding the discussion that follows.

In accordance with the present invention there may be employed conventional molecular biology, microbiology, and recombinant DNA techniques within persons skilled in the art. Such techniques are explained fully in the literature.

"Wounds" can be characterized as open wounds and closed wounds. Open wounds can be classified into a number of different types, including incisions (caused by a clean, sharp-edged object such as a knife or a razor), lacerations (rough, irregular wounds caused by crushing or ripping forces), abrasions or grazes (a superficial wound in which the topmost layers of the skin are scraped off, often caused by a sliding fall onto a rough surface), and puncture wounds (caused by an object puncturing the skin, such as a nail or needle). Closed wounds have far fewer categories, but are just as dangerous as open wounds. They are contusions or bruise (caused by blunt force trauma that damages tissues under the skin), hematoma (caused by damage to a blood vessel that in turn causes blood to collect under the skin) and crushing injuries (caused by a great or extreme amount of force applied over a long period of time).

The "wound healing" process has 3 phases. They are the inflammatory phase, the proliferative phase, and the maturational phase.

The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, potent vasoconstrictors. This initial response helps to limit hemorrhage. After a short period, capillary vasodilatation occurs secondary to local histamine release, and the cells of inflammation are able to migrate to the wound bed. The inflammatory phase continues, and more immune response cells migrate to the wound. The second response cell to migrate to the wound, the neutrophil, is responsible for debris scavenging, complement-mediated opsonization of bacteria, and bacteria destruction via oxidative burst mechanisms (ie, superoxide and hydrogen peroxide formation). The neutrophils kill bacteria and decontaminate the wound from foreign debris.

The second stage of wound healing is the proliferative phase. Epithelialization, angiogenesis, granulation tissue formation, and collagen deposition are the principal steps in this anabolic portion of wound healing. Epithelialization occurs early in wound repair. If the basement membrane remains intact, the epithelial cells migrate upwards in the normal pattern. This is equivalent to a first-degree skin burn. The epithelial progenitor cells remain intact below the wound, and the normal layers of epidermis are restored in 2-3 days. If the basement membrane has been destroyed, similar to a second- or third-degree burn, then the wound is reepithelialized from the normal cells in the periphery and from the skin appendages, if intact (eg, hair follicles, sweat glands). The final part of the proliferative phase is granulation tissue formation. Fibroblasts differentiate and produce ground substance and then collagen. The ground substance is deposited into the wound bed; collagen is then deposited as the wound undergoes the final phase of repair. Many different cytokines are involved in the proliferative phase of wound repair. The steps and the exact mechanism of control have not been elucidated. Some of the cytokines include PDGF, insulinlike growth factor (IGF), and EGF. All are necessary for collagen formation.

The final phase of wound healing is the maturational phase. The wound undergoes contraction, ultimately resulting in a smaller amount of apparent scar tissue. The entire process is a dynamic continuum with an overlap of each phase and continued remodeling. The wound reaches maximal strength at one year, with a tensile strength that is 30% of normal skin. Collagen deposition continues for a prolonged period, but the net increase in collagen deposition plateaus after 21 days.

"Angiogenesis" is generally thought to be heavily regulated by growth factors and other ligands. Angiogenesis, and the concurrent tissue development and regeneration, depends on the tightly controlled processes of endothelial cell proliferation, migration, differentiation and survival. Both stimulator and inhibitor ligands appear to interact, directly or indirectly, with cellular receptors during these processes. Angiogenesis begins with the erosion of the basement membrane by enzymes released by endothelial cells and leukocytes. The endothelial cells, which line the lumen of blood vessels, then protrude through the basement membrane. Angiogenic stimulators induce endothelial cells to migrate through the eroded basement membrane. The migrating cells then form a "sprout" off the parent blood vessel, where the endothelial cells undergo mitosis and proliferate. The endothelial sprouts merge with each other to form capillary loops, creating the new blood vessel.

As used herein "burn" is the injury resulting from exposure to heat, electricity, radiation (for example, sunburn and laser surgery), or caustic chemicals.

"Diabetes mellitus" is a group of metabolic diseases characterized by high bloodsugar (glucose) levels, which result from defects in insulin secretion, or action, or both. Diabetes mellitus, commonly referred to as diabetes, means "sweet urine." Elevated levels of blood glucose (hyperglycemia) lead to spillage of glucose into the urine, hence the term sweet urine. Normally, blood glucose levels are tightly controlled by insulin, a hormone produced by the pancreas. Insulin lowers the blood glucose level. When the blood glucose elevates (for example, after eating food), insulin is released from the pancreas to normalize the glucose level. In patients with diabetes mellitus, the absence or insufficient production of insulin causes hyperglycemia. Diabetes mellitus is a chronic medical condition, meaning it can last a lifetime.

Diabetes can sometimes lead to peripheral neuropathy which, particularly when combined with damaged blood vessels, can lead to foot ulcers, and possibly progressing to necrosis, infection and gangrene, sometimes requiring limb amputation.

A "nucleic acid" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA molecule that has undergone a molecular biological manipulation.

"Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

As used herein the term "nucleic acid fragment" is intended to indicate any nucleic acid molecule of cDNA, genomic DNA, synthetic DNA or RNA origin. The term "fragment" is intended to indicate a nucleic acid segment which may be single- or double-stranded, and which may be based on a complete or partial naturally occurring nucleotide sequence encoding a polypeptide of interest. The fragment may optionally contain other nucleic acid segments.

The nucleic acid fragment of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction.

As used herein the term "plasmid vaccines" are defined as purified preparations of plasmid DNA designed to contain a gene or genes for the intended vaccine antigen as well as genes incorporated into the construct to allow for production in a suitable host system.

EXAMPLES

The examples below are non-limiting and are merely representative of various aspects and features of the present invention.

Example 1

Effect of TMD23 on HaCaT Epithelial Cell Migration

Figure 1:
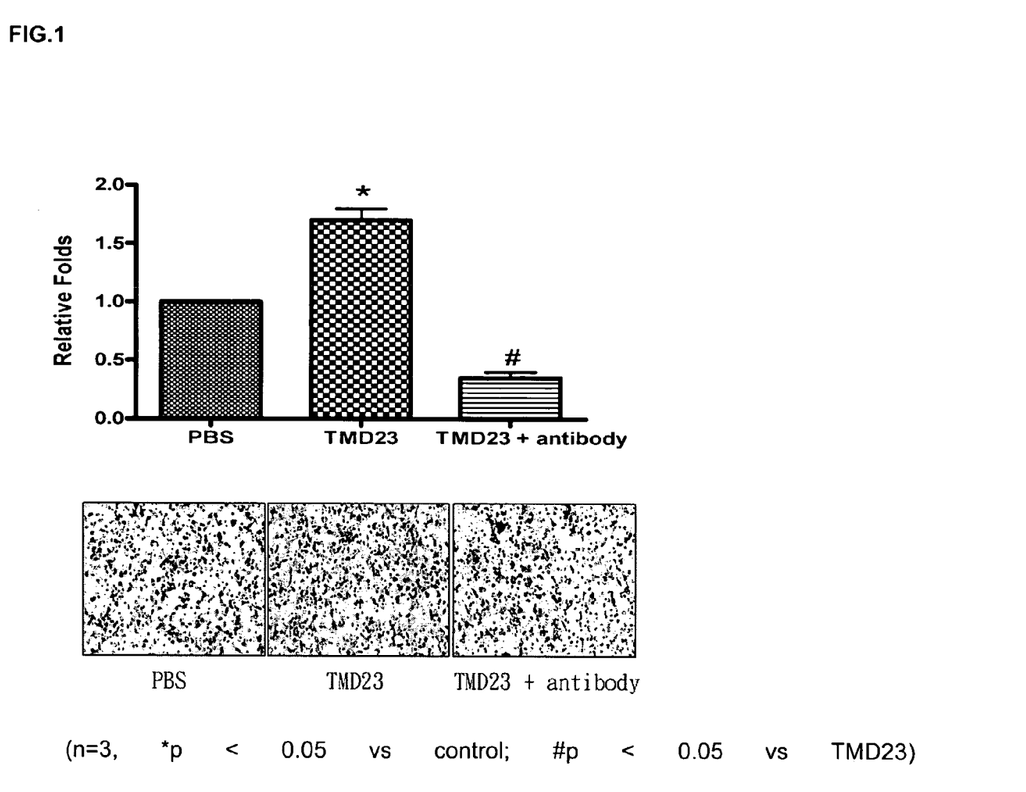
FIG. 1 shows the effect of TMD23 on HaCaT epithelial cell migration.

The effect of TMD23 on the migration of HaCaT cells was evaluated using Boyden chamber with 6.5-mm-diameter polycarbonate filters (8-μm pore size). The lower filter surface was coated with collagen type IV. TMD23 (100 ng/ml) or TMD23 (100 ng/ml) plus anti-TM antibody (1 μg/ml) was added in the DMEM in the lower wells. Cell suspension (50 μL) containing $1 \times 10^4$ cells was loaded into each upper well. The number of the cells migrated through the membrane in eight hours was counted under microscope after fixed with methanol and stained with 10% GIEMSA. As shown in FIG. 1, TMD23 markedly induced chemotactic migration in HaCaT cells.

Example 2

Materials

DMAp was 100 μg of the recombinant TMD23 purified protein (residues Ala242-Ser515 of SEQ ID NO:2) in 20 μl of 0.5% CMC/PBS solution. The 0.5% CMC (Carboxymethylcellulose)/PBS (Phosphate Buffered Saline) at pH 7.4 was used as the vehicle in solution form for DMAp and CGS-21680. CGS-21680 hydrochloride (2-p-[2-Carboxyethyl] phenethylamino-5'-N-ethylcarboxamidoadenosine) was a G-protein activator and was purchased from Sigma-Aldrich.

DMAc gel was 100 μg of the recombinant TMD23 purified protein (residues Ala242-Ser515 of SEQ ID NO:2) in 20 mg of base gel. The base gel was used as a negative control of DMAc gel and Regranex gel. The base gel was composed of sodium carboxymethylcellulose, sodium chloride, sodium acetate trihydrate, glacial acetic acid, methylparaben, propylparaben, m-Cresol 1-lysine hydrochloride, benzyl alcohol, methylchloroisothiazoline, methylisothiazolinine, ammonium acryloyldimethyltaurateNP copolymer and water for injection. Regranex gel was purchased form Johnson & Johnson.

For the chemicals used in the examples, 10% buffered neutral formalin solution (Shiyak Kogyo, Japan), carboxymethylcellulose (Sigma-Aldrich, USA), GCS-21680 hydrochloride (Tocris, USA), hexobarbital (Sigma-Aldrich, USA), phosphate buffered saline (PBS pH 7.4, Sigma-Aldrich, USA) and sodium chloride (Wako, Japan) were used.

As for the equipments used in the examples, animal cage (Allentown, USA), Image—ProPlus (Media Cybernetics, Version 4.5.29), pipetman (Gilson, Germany) and sharp punch, internal diameter of 12 mm (Sinter, R. O. C.) were used.

Example 3

Animals

Male CD-1 (Crl.) derived mice weighing 24±2 g were provided by BioLasco Taiwan (under Charles River Laboratories Technology Licensee). Space allocation for 10 animals was 29×18×13 cm. All animals were maintained in a controlled temperature (22° C.-24° C. and humidity (50%-60%) environment with 12 hours light dark cycles for at least one week in MDS Pharma Services—Taiwan Laboratory prior to use. Free access to standard lab chow for mice [MF-18 (Oriental Yeast Co., Ltd., Japan)] and RO water was granted. All aspects of this work including housing, experimentation and disposal of animals were performed in general accordance with the Guide for the Care and Use of Laboratory Animals (National Academy Press, Washington, D.C., 1996).

Non-insulin dependent diabetic mellitus (NIDDM) male mice (C57BLKS/J-m+/+Lepr db), weighing 50±5 g (9 weeks of age), were provided by Institute for Animal Reproduction (IAR, Japan) were used. These animals exhibit hyperinsulinemia, hyperglycemia and islet atrophy. The animals were housed in Individually Ventilated Cages racks (IVC Racks, 36 Mini Isolator systems) under Specific Pathogen-Free (SPF) condition throughout the experiment. Each APEC_cage (in cm, 26.7 length×20.7 width×14.0 height) was sterilized with autoclave and contained 7 mice, and the animals were then maintained in a hygienic environment under controlled temperature (22°-24° C.) and humidity (50%-60%) with 12-hour light/dark cycle. The animals were given free access to sterilized lab. chow and sterilized distilled water adlibitum. All aspects of this work, i. e. housing, experimentation and disposal of animals, are performed in general accordance with the Guide for the Care and Use of Laboratory Animals (National Academy Press, Washington, D.C., 1996).

Example 4

TMD23 Accelerates Wound Closure in Mice

Figure 2:
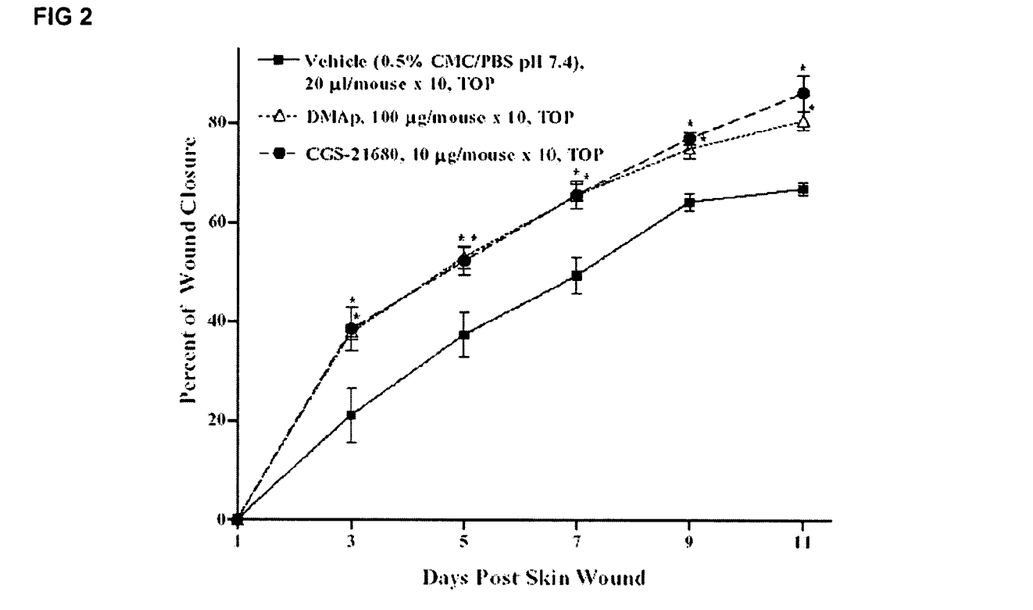
FIG. 2 is a time course of wound closure in CD-1 mice treated with DMAp or CGS-21680 (in solution form) by topical application. Test substance and vehicle were each administered topically once daily for 10 consecutive days. CGS-21680 (10 µg/mouse) as a positive control was administered topically at the same timing. The wound closure (%) and the wound half-closure time (CT50) were determined and One-way ANOVA followed by Dunnett's test was applied for comparison between the treated and its corresponding vehicle groups on days 3, 5, 7, 9 and 11.
Figure 3:
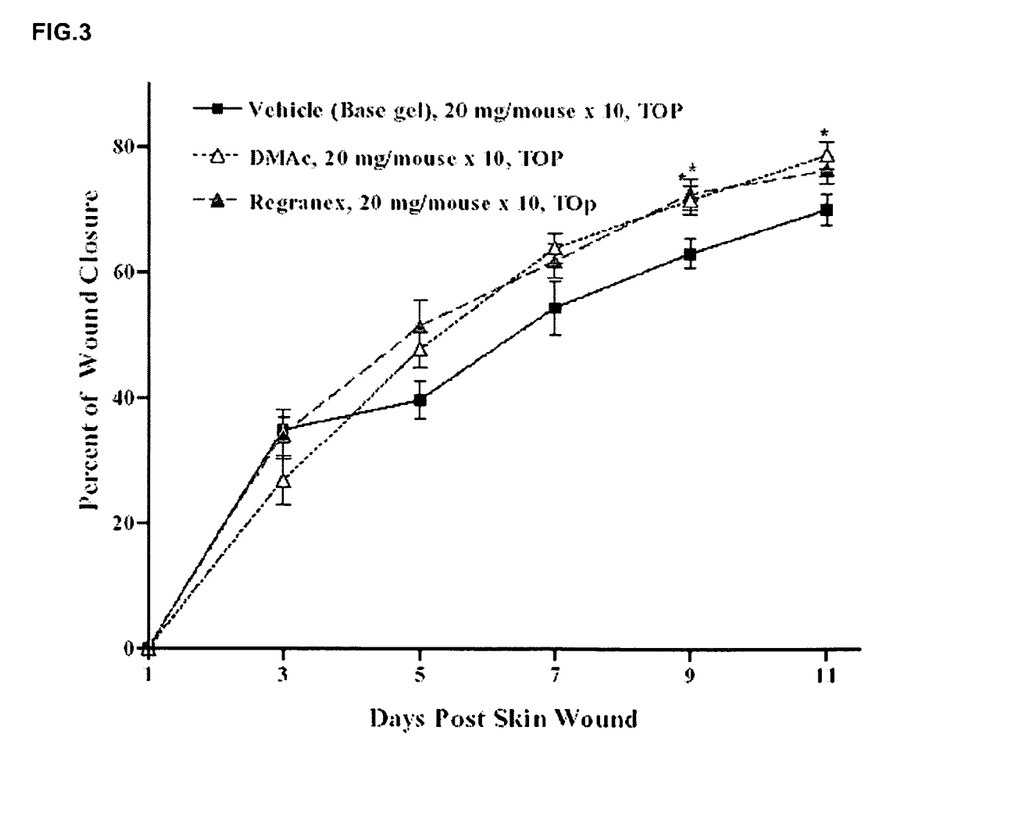
FIG. 3 is a time course of wound closure in CD-1 mice treated with DMAc or Regranex (in gel form) by topical application. Test substances were each administered topically once daily for 10 consecutive days. The wound closure (%) and the wound half-closure time (CT50) were determined and One-way ANOVA followed by Dunnett's test was applied for comparison between the treated and its corresponding vehicle groups on days 3, 5, 7, 9 and 11.

Groups of 5 CD-1 (Crl.) derived male mice each weighing 24±2 g were used. During testing period, the animals were singly housed in individual cages. Under hexobarbital (90 mg/kg, IP) anesthesia, the shoulder and back region of each animal was shaved. A sharp punch (ID 12 mm) was applied to remove the skin including *panniculus camosus* and adherent tissues. DMAc, Regranex and Base gel at 20 mg/mouse and DMAp at 100 µg/mouse as well as the vehicle (0.5% CMC/PBS pH 7.4, 20 µl/mouse) and CGS-21680 at 10 µg/mouse as the positive control were each administered topically (TOP) immediately following cutaneous injury once daily for 10 consecutive days. The wound area, traced onto clear plastic sheets, was measured by use of an Image—ProPlus (Media Cybernetics, Version 4.5.29) on days 1, 3, 5, 7, 9 and 11. The percent closure of the wound (%) was calculated, and wound half-closure time (CT50) was analyzed by linear regression using Graph-Prism (Graph Software USA). One-way ANOVA followed by Dunnett's test was applied for comparison between the treated and its corresponding vehicle groups at each measurement time point. Differences are considered statistically significant at P<0.05. CGS-21680 (10 µg/mouse×10) as the positive standard exhibited significant increase (P<0.05) in wound closure (on days 3, 5, 7, 9 and 11) with decreased CT50 relative to corresponding vehicle control values. The results are summarized in FIG. 2 (in solution phase), FIG. 3 (in gel phase) and Table. 1 below:

It is concluded that DMAp (100 µg/mouse) demonstrated most persistent effect on wound healing throughout the study with a significant reduction in CT50 value; DMAc and Regranex tended to promote wound healing but without significant effect on CT50; Base gel was without any effect in the mouse cutaneous wound model.

Example 5

TMD23 Accelerates Wound Closure in Mice with Diabetes

Figure 4:
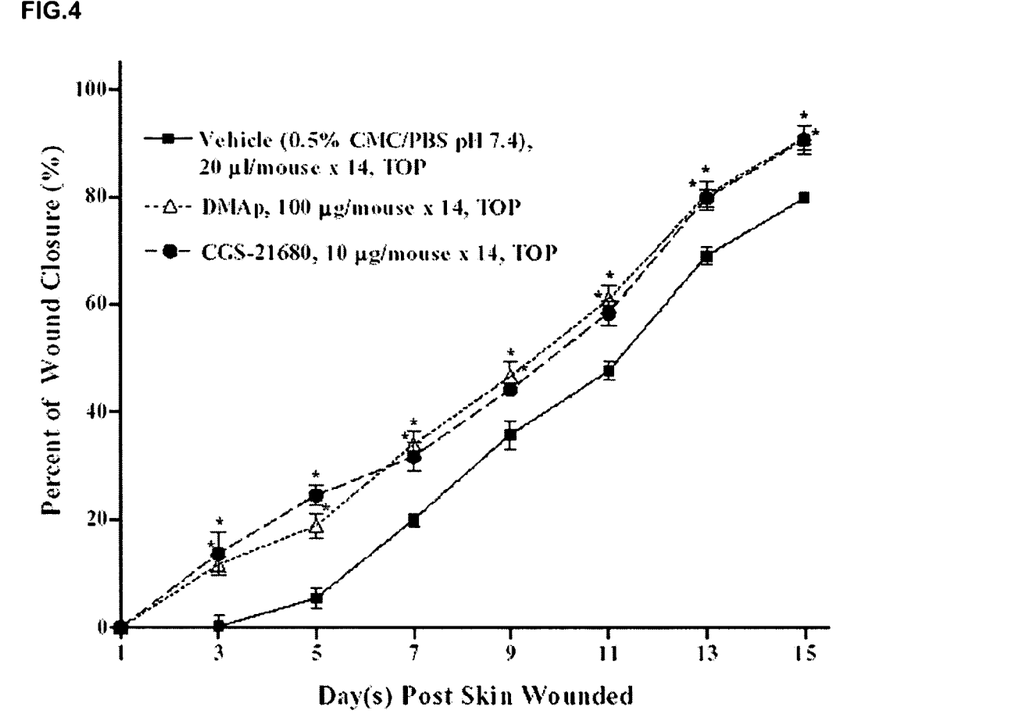
FIG. 4 is a time course of wound closure in diabetic mice (Lepr db) treated with DMAp or CGS-21680 (in solution form) by topical application. Test substance and vehicle were each administered topically once daily for 14 consecutive days. CGS-21680 (10 µg/mouse) as a positive control was administered topically at the same timing. The wound closure (%) and the wound half-closure time (CT50) were determined and One-way ANOVA followed by Dunnett's test was applied for comparison between the treated and its corresponding vehicle groups on days 3, 5, 7, 9, 11, 13 and 15.
Figure 5:
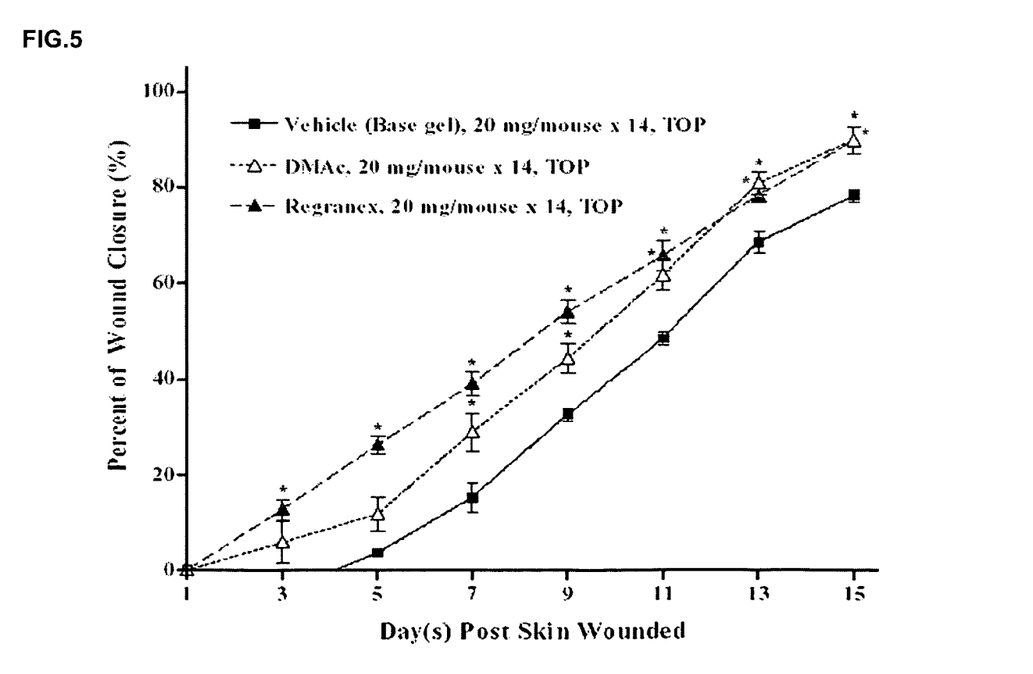
FIG. 5 is a time course of wound closure in diabetic mice (Lepr db) treated with DMAc or Regranex (in gel form) by topical application. Test substances were each administered topically once daily for 14 consecutive days. The wound closure (%) and the wound half-closure time (CT50) were determined and One-way ANOVA followed by Dunnett's test was applied for comparison between the treated and its corresponding vehicle groups on days 3, 5, 7, 9, 11, 13 and 15.

Groups of 5 C57BLKS/J-m+/+Lepr db male mice weighing 50±5 g were used. During testing period, the animals were singly housed in Individually Ventilated Cages Racks (IVC Racks, 36 Mini Isolator Systems). Under hexobarbital (90 mg/kg, IP) anesthesia, the shoulder and back region of each animal were shaved. A sharp punch (ID 12 mm) was applied to remove the skin including *panniculus carnosus* and adherent tissues. The wound area, traced onto clear plastic sheets on days 1, 3, 5, 7, 9, 11, 13 and 15, was measured by use of an image-analyzer (ProPlus, Media Cybernetics, V4.5.29). Test substances in solution or gel form and vehicle, positive control CGS-21680 or Regranex were each applied topically starting on day 1, immediately after wound injury, once daily for a total of 14 consecutive days. Test substances DMAp (100 µg/mouse), vehicle (0.5% CMC/PBS pH 7.4) and CGS-21680 (10 µg/mouse) are in solution form and dosing volume at 20 µl/mouse was used. Meanwhile, DMAc, Regranex and Base gel (as vehicle control group) are in gel form and were administered at 20 mg/mouse. The half-closure time (CT50) for the wound was determined by linear regression using Graph-Pad Prism (Graph Pad Software USA) and One-way ANOVA followed by Dunnett's test was applied for comparison between the treated and vehicle groups at each measurement time point. Differences are considered of statistical significance at P<0.05 level. CGS-21680 (10 µg/mouse×14) and Regranex (20 mg/mouse×14) as the positive control substance caused significant increase (P<0.05) in percent of wound closure (on days 3, 5, 7, 9, 11, 13 and 15) and a significant decrease in CT50 relative to corresponding vehicle control values. The results are summarized in FIG. 4 (in solution phase), FIG. 5 (in gel phase) and Table. 2 below:

TABLE 1

The effect of test articles on closure of wound and half-closure time in CD-1 mice

| Treatment | Route | Dose | | The Closure of Wound (%) | | | | | $CT_{50}$ (Days) |
|---|---|---|---|---|---|---|---|---|---|
| | | | | Day 3 | Day 5 | Day 7 | Day 9 | Day 11 | |
| Vehicle | TOP | 20 µl/mouse × 10 | X | 21.1 | 37.5 | 49.3 | 64.1 | 66.8 | 7.5 |
| | | | SEM | 5.6 | 4.6 | 3.6 | 1.8 | 1.2 | 0.4 |
| DMAp | TOP | 100 µg/mouse × 10 | X | 37.9* | 53.0* | 65.4* | 74.8* | 80.5* | 5.7* |
| | | | SEM | 1.6 | 2.2 | 2.5 | 2.0 | 2.0 | 0.2 |
| CGS-21680 | TOP | 10 µg/mouse × 10 | X | 38.5* | 52.2* | 65.5* | 76.9* | 86.1* | 5.6* |
| | | | SEM | 4.4 | 2.7 | 2.7 | 1.3 | 3.6 | 0.3 |
| Base gel | TOP | 20 mg/mouse × 10 | X | 35.1 | 39.8 | 54.5 | 63.2 | 70.3 | 7.0 |
| | | | SEM | 2.1 | 3.0 | 4.2 | 2.4 | 2.6 | 0.3 |
| DMAc | TOP | 20 mg/mouse × 10 | X | 27.0 | 47.8 | 64.0 | 71.7* | 79.0* | 6.2 |
| | | | SEM | 3.8 | 2.8 | 2.4 | 2.3 | 2.1 | 0.2 |
| Regranex | TOP | 20 mg/mouse × 10 | X | 34.3 | 51.5 | 61.9 | 72.7* | 76.6 | 6.1 |
| | | | SEM | 3.9 | 4.3 | 2.7 | 2.5 | 2.1 | 0.3 |

The closure of the wound (%) and wound half-closure time ($CT_{50}$) were determined and One-way ANOVA followed by Dunnett's test was used for comparison between the treated and its corresponding vehicle groups.
*P < 0.05, vs. vehicle control.

TABLE 2

The effect of test articles on closure of wound and half-closure time in Lepr db Mice

| Treatment | Route | Dose | | Day 3 | Day 5 | Day 7 | Day 9 | Day 11 | Day 13 | Day 15 | $CT_{50}$ (Days) |
|---|---|---|---|---|---|---|---|---|---|---|---|
| Vehicle | TOP | 20 μl/mouse × 14 | X | 0.2 | 5.5 | 20.0 | 35.8 | 47.7 | 69.1 | 79.8 | 10.8 |
| (0.5% CMC) | | | SEM | 2.0 | 1.9 | 1.2 | 2.7 | 1.7 | 1.6 | 0.8 | 0.2 |
| DMAp | TOP | 100 μg/mouse × 14 | X | 11.7* | 18.9* | 33.9* | 46.7* | 61.0* | 80.4* | 91.1* | 9.1* |
| | | | SEM | 1.5 | 2.2 | 2.6 | 2.8 | 2.5 | 2.7 | 2.3 | 0.2 |
| CGS-21680 | TOP | 10 μg/mouse × 14 | X | 13.7* | 24.5* | 31.7* | 44.3* | 58.5* | 79.8* | 90.7* | 9.1* |
| | | | SEM | 3.9 | 1.9 | 2.6 | 0.9 | 2.2 | 1.7 | 2.7 | 0.2 |
| Base gel | TOP | 20 mg/mouse × 14 | X | −4.4 | 3.7 | 15.3 | 32.7 | 48.6 | 68.7 | 78.3 | 11.1 |
| | | | SEM | 5.3 | 4.1 | 3.0 | 1.3 | 1.4 | 2.3 | 1.3 | 0.1 |
| DMAc | TOP | 20 mg/mouse × 14 | X | 5.9 | 11.8 | 29.0* | 44.5* | 61.8* | 81.0* | 89.9* | 9.4* |
| | | | SEM | 4.3 | 3.6 | 4.0 | 3.0 | 3.2 | 2.4 | 2.8 | 0.3 |
| Regranex | TOP | 20 mg/mouse × 14 | X | 12.8* | 26.3* | 39.1* | 54.1* | 65.8* | 78.5* | 89.7* | 8.6* |
| | | | SEM | 2.2 | 1.8 | 2.5 | 2.4 | 3.1 | 1.4 | 1.0 | 0.2 |

The closure of the wound (%) and wound half-closure time ($CT_{50}$) were determined and One-way ANOVA followed by Dunnett's test was used for comparison between the treated and its corresponding vehicle groups.
*$P < 0.05$, vs. vehicle control.

concluded that DMAp (100 μg/mouse), DMAC and Regranex (each 20 mg/mouse), and CGS-21680 (10 μg/mouse) demonstrated persistent augmenting effect on wound healing throughout the study with a significant reduction in CT50 value. At early phase, Vehicle of Base gel seemed to have a slight delay in wound healing compared with vehicle of 0.5% CMC/PBS pH 7.4.

Example 6

TMD23 Reduces Evaporation Rate from the Wound Opening

Figure 6:
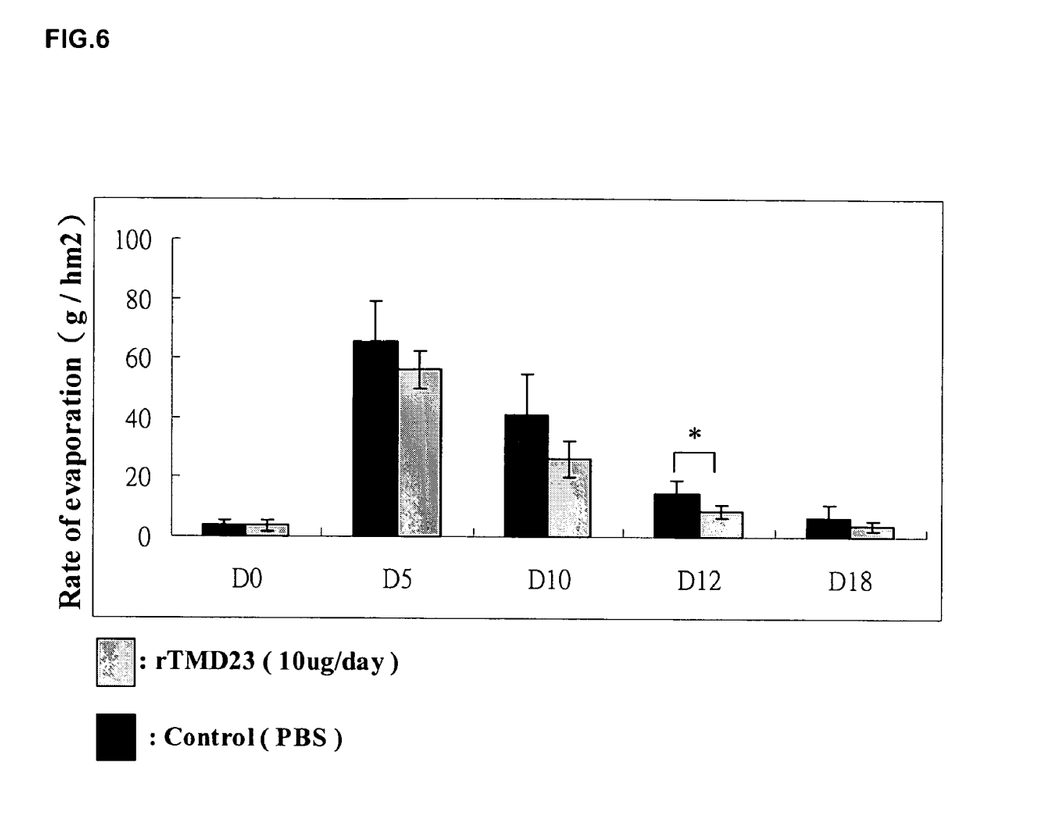
FIG. 6 shows that TMD23 reduces evaporation rate from the wound opening.

To measure the rate of epithelialization, the rate of water evaporation from the wound area was measured using TM210 Tewameter (COURAGE+KHAZAKA electronic Co., Cologne, Germany). Lower level of evaporation rate is representative of higher level of epithelialization or keratinization. The results (FIG. 6) showed that TMD23 could effectively increase the rate of epithelialization of the wound.

One skilled in the art readily appreciates that the present invention is well adapted to carry out the objects and obtain the ends and advantages mentioned, as well as those inherent therein. The cell lines, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for accelerating closure of an open wound in the skin of a patient, comprising administering to the open wound in the skin of the patient in need thereof a composition comprising:
(a) a polypeptide consisting of the amino acids Ala242 to Ser515 of human thrombomodulin (SEQ ID NO: 2) in an effective amount; and
(b) a pharmaceutically acceptable vehicle, thereby accelerating closure of the open wound in the skin of the patient.

2. The method of claim 1, wherein the open wound results from an incision, a laceration, an abrasion, a puncture wound, a blister, a skin tear, a donor or graft site, acne, a hematoma, a crushing injury, an injury caused by dermabrasion, and an injury caused by laser resurfacing.

3. The method of claim 1, wherein the open wound comprises a diabetic foot ulcer.

4. The method of claim 1, wherein the open wound extends to the subcutaneous tissue panniculus carnosus.

5. The method of claim 1, wherein the open wound in the skin of the patient is a surgical wound.

6. The method of claim 1, wherein the composition is a gel, a cream, a paste, a lotion, a spray, a suspension, a solution, a dispersion salve, a hydrogel or an ointment formulation.

7. The method of claim 6, wherein the composition is administered to the patient topically, or via injection.

8. The method of claim 1, further comprising the step of allowing the polypeptide to cause epithelialization of the open wound, and thereby accelerating closure of the open wound of the patient.

9. The method of claim 1, wherein the composition is a solution or gel formulation.

10. A method for accelerating healing of a wound in a subcutaneous tissue of a patient, comprising administering to the wound in the subcutaneous tissue of the patient in need thereof a composition comprising:
(a) a polypeptide consisting of the amino acids Ala242 to Ser515 of human thrombomodulin (SEQ ID NO: 2) in an effective amount; and
(b) a pharmaceutically acceptable vehicle,
thereby accelerating healing of the wound in the subcutaneous tissue of the patient.

11. The method of claim 10, wherein the subcutaneous tissue is panniculus carnosus.

12. The method of claim 10, wherein the wound comprises a diabetic foot ulcer.

13. The method of claim 10, wherein the wound extends to the subcutaneous tissue panniculus carnosus and adherent tissues.

14. The method of claim 10, further comprising allowing the polypeptide to cause epithelialization of the wound, and thereby accelerating healing of the wound in the subcutaneous tissue of the patient.

15. The method of claim 10, wherein the wound in the subcutaneous tissue of the patient is a skin contusion.

16. A method for accelerating closure of an open wound in a diabetic, comprising administering to the diabetic in need thereof a composition comprising:
(a) a polypeptide consisting of the amino acids Ala242 to Ser515 of human thrombomodulin (SEQ ID NO: 2) in an effective amount; and
(b) a pharmaceutically acceptable vehicle.

17. The method of claim 16, wherein the wound comprises a diabetic foot ulcer.

* * * * *